United States Patent [19]
Krapcho et al.

[11] Patent Number: 5,587,382
[45] Date of Patent: Dec. 24, 1996

[54] 6,9-BIS[(2-AMINOETHYL) AMINO]BENZO [G]ISOQUINOLINE-5,10- DIONE DIMALEATE; AN AZA-ANTHRACENEDIONE WITH REDUCED CARDIOTOXICITY

[75] Inventors: A. Paul Krapcho, Shelburne; Miles P. Hacker, Williston, both of Vt.; Ennio Cavalletti, Monza; Ferdinando C. Giuliani, Cassina de Pecchi, both of Italy

[73] Assignee: Boehringer Mannheim Italia, SpA, Monza, Italy

[21] Appl. No.: 467,874

[22] Filed: Jun. 6, 1995

Related U.S. Application Data

[63] Continuation-in-part of Ser. No. 218,946, Mar. 28, 1994, abandoned.

[51] Int. Cl.$^6$ .................................................. A61K 31/44
[52] U.S. Cl. ................................................................. 514/290
[58] Field of Search ................................................ 514/290

[56] References Cited

FOREIGN PATENT DOCUMENTS 9215300 of 1992 WIPO ..................................... 514/296

Primary Examiner—Jerome D. Goldberg
Attorney, Agent, or Firm—Nikaido, Marmelstein, Murray & Oram, LLP

[57] ABSTRACT

In the search for novel heteroanalogs of anthracenediones, 6,9-bis[(2-aminoethyl-amino]-benzo[g]isoquinoline-5,10-dione dimaleate (BBR 2778), was selected as the most promising compound. Toxicological studies indicate that BBR 2778 is not cardiotoxic.

4 Claims, 2 Drawing Sheets

Cyclic voltammetry of BBR 2778 (6,9-bis[(2aminoethyl)amino] benzo [g] isoquinoline-5,10-dione dimaleate salt

6,9-BIS[(2-AMINOETHYL) AMINO]BENZO [G]ISOQUINOLINE-5,10- DIONE DIMALEATE; AN AZA-ANTHRACENEDIONE WITH REDUCED CARDIOTOXICITY

This application is a CIP of Ser. No. 08/218,946, filed Mar. 28, 1994, now abandoned.

BACKGROUND

FIELD OF THE INVENTION

The anthracycline antibiotics doxorubicin and daunorubicin possess outstanding antitumor activity and are recognized as two of the most important cancer chemotherapeutic drugs available. However, these drugs are quite toxic. In addition to producing stomatitis, alopecia and bone marrow depression, they often cause severe cumulative and irreversible cardiac toxicity which can be fatal.

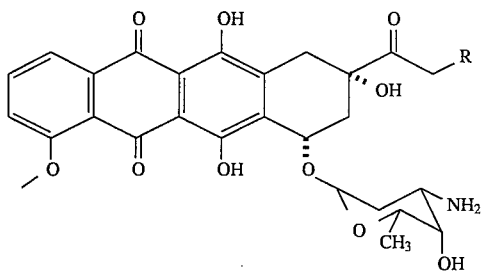

(I) R = H daunorubicin
(II) R = OH doxorubicin

Numerous investigators have attempted to design related drugs which maintain the biological activity, but do not possess the cardiotoxicity of the anthracyclines.

Random screening of a vast number of compounds provided by the Allied Chemical Company, at the National Cancer Institute led to the discovery of ametantrone as having significant antitumor activity. Further investigation by Cheng regarding the rational development of analogs of ametantrone through structure-activity studies of some substituted aminoalkyl aminoanthraquinones led to the synthesis of mitoxantrone which exhibited marked antitumor activity. An independent development of mitoxantrone has also been reported by Murdock.

Mitoxantrone was considered as an analog of doxorubicin with less structural complexity but with a similar mode of action. In vitro screening systems showed mitoxantrone to have higher efficacy than doxorubicin at equivalent concentrations. In clinical studies, mitoxantrone has ben,shown to be effective against numerous types of tumors with far less toxic side effects than those resulting from doxorubicin therapy.

Mitoxantrone is currently gaining an important place in the clinical management of leukemias and lymphomas as well as in combination therapy of advanced breast and ovarian cancers. Although mitoxantrone is endowed with an improved tolerability profile compared with doxorubicin and other anthracyclines, this drug is not devoid of significant toxic side effects, especially those associated with myelosuppression and cardiotoxicity. Moreover, congestive heart failure is a serious clinical concern, particularly in patients previously treated with anthracyclines. (Faulds, D.; Balfour, J. A.; Chrisp, P.; Langtry, H. D., Mitoxantrone, a Review of its Pharmacodynamic and Pharmacokinetic Properties, and Therapeutic Potential in the Chemotherapy of Cancer, Drugs 1991, 41, 400–449).

The mechanisms of action of ametantrone and mitoxantrone are not yet well defined. Many studies suggest that intercalation into DNA is a major cellular event. This intercalative interaction may serve as an anchor for the drugs at specific base pair sites of the DNA followed by the critical cell-killing events. Nucleic acid compaction and interference with the DNA topoisomerase II activity resulting in protein associated-DNA strand breaks have also been proposed as critical, events (common also to a number of other antineoplastic agents) which lead to mitoxantrone induced cell death. Cellular destruction by antitumor anthracene-9, 10-diones, including mitoxantrone, has also been attributed to oxidative metabolism which results in the formation of free radicals capable of DNA alkylation and/or DNA scission, yielding non-protein associated DNA strand breaks. Recent studies suggest that enzymes such as NADPH (quinone acceptor) oxidoreductase can reduce mitoxantrone to reactive hydroxyl radicals. However, it is generally believed that quinone reduction is probably more related to the cardiotoxic side effects of mitoxantrone than to the mechanism of its antitumor activity. The cardiotoxicity of mitoxantrone and doxorubicin has also been associated with the metal chelating ability of the adjacent hydroxyl and quinone groups. Formation of drug-metal complexes could enhance oxidation-reduction cycling by a metal catalyzed type reaction.

Non-hematological side effects from mitoxantrone treatment are mild compared to side effects of doxorubicin treatment. Although mitoxantrone shows diminished cardiotoxicity when compared to doxorubicin, clinical trials indicate that mitoxantrone is not totally free of cardiotoxicity.

The cardiotoxic effects of the anthracyclines and the anthracene diones are probably multimodal. One important effect is thought to be the peroxidation of cell membrane lipids; the lower incidence of cardiotoxicity associated with mitoxantrone than with doxorubicin is ascribed to the diminished rate of superoxide radical $O_2.^-$ formation. The metabolic reduction of mitoxantrone, by NADPH in human liver, to the free radical occurs at a low enough rate that it does not result in a significant increase in microsomal $O_2.^-$ formation.

Significant evidence has accumulated which strongly suggests anthracycline semiquinone free radicals and oxygen radicals as major contributors to cardiac toxicity. Many anticancer agents containing a quinone group have been found to be enzymatically reduced to the semiquinone free radical by NADPH-cytochrome reductase. The semiquinone is then incorporated into a redox cycle which involves further catalytic NADPH oxidation and oxygen consumption. Molecular oxygen is reduced by the semiquinone free radical to superoxide anion radicals which can go on to form hydroxyl radicals. Superoxide anion radicals and other reactive oxygen species including hydrogen peroxide, singlet oxygen and hydroxyl radicals are well known to attack unsaturated membrane lipids resulting in lipid peroxidation. This lipid peroxidation is believed to be the cause of anthracycline induced cardiotoxicity. The cardiac tissue is particularly susceptible to damage by lipid peroxidation because cardiac tissue contains lower levels of several enzymes (catalase, superoxide dismutase, and glutathione peroxidase) involved in protection against such damage.

The potential chemotherapeutic utility of mitoxantrone which was evident from the in vivo trial results has warranted further development with the drug. A number of structurally modified analogs of mitoxantrone have since been synthesized and structure-activity relationship studies made.

BACKGROUND RELATING TO OTHER ANTHRACENE COMPOUNDS

The antitumor agents ametantrone (III) and mitoxantrone (IV), belonging to the class of 1,4-bis(aminoalkylamino)anthracene-9,10-diones, are further representative examples of quinone containing anticancer agents. Although mitoxantrone is endowed with an improved tolerability profile compared with doxorubicin and other anthracyclines, this drug is not devoid of significant toxic side effects, especially those associated with myelosuppression and cardiotoxicity.

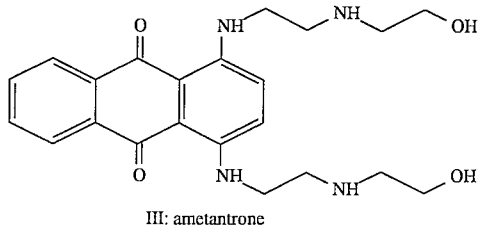

III: ametantrone

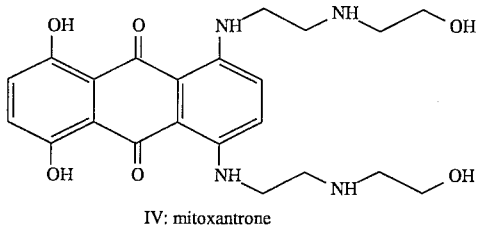

IV: mitoxantrone

Histologically mitoxantrone induces a high incidence of focal myocardial damage in mice similar to that observed with doxorubicin and has a spectrum of myocardial activity similar to that of doxorubicin (Perkins, W. E. et al., Myocardial Effects of Mitoxantrone and Doxorubicin in the Mouse and Guinea Pig, Cancer Treat. Reports, 68, 841–7, (1984)).

The biochemical basis for the high incidence of cardiotoxicity observed with mitoxantrone and anthracyclines is not yet fully understood. Several different hypotheses connect such a toxicity with different biochemical phenomena. The production of these free radicals is strictly connected with the capacity of quinone anticancer agents to be reduced to semiquinone free radicals. These latter compounds are capable of donating electrons to molecular oxygen, thus forming superoxide radical leading to peroxidative damage of cardiac tissue which is more susceptible to peroxidative damage because of lowered concentrations of detoxifying enzymes (catalase, superoxide dismutase and glutathione peroxidase).

Attempts have been made to produce less cardiotoxic second generation anthracyclines and anthracenediones. The general strategy of such research is the preparation of chromophore modified synthetic analogues in which the reduction of the quinone is rendered more difficult. In fact, the more difficult is the reduction of the quinone, the lower is the production of oxygen free radicals. This can be achieved by rendering the redox potential of the quinone sub-unit more negative, i.e., rendering more difficult the electron addition. Chromophore modified synthetic analogues are designed to be more resistant to enzymatic reduction, while retaining the planar and spatial characteristics of the parent prototypes necessary for molecular recognition and DNA binding (Showalter, H. D. H. et al., Design, Biochemical Pharmacology, Electrochemistry and Tumor Biology of Antitumor Anthrapyrazoles, Anti-cancer Drug Design, 1, 73–85, (1986)). Several heteroanalogues of anthracyclines have been reported such as: indole analogues (Kita, Y. et al., J. Chem. Soc. Chem. Comm., 1474, (1987)); thiophene analogues (Kita, Y. et al., Tetrahedron Letters, 28, 3971(1987)); pyridino and pyrazino analogues (Kita, Y. et al., Chem. Pharm. Bull. 39, 857, (1991)); and Xantho[2,3-g]tetralines (Lown, J.; Sondhi, S., J. Org. Chem., .50, 1413–1418, (1985)). Further heteroanalogues of anthracyclines are reported in Eur. Pat. App. 17,469,15 (Oct. 15, 1980). 5-iminodaunorubicin (V) (Lown, J. W. et al., Biochem. Pharmacol., 31, 575–581, (1982)) is an example of modified anthracycline in which the quinone sub-unit is altered.

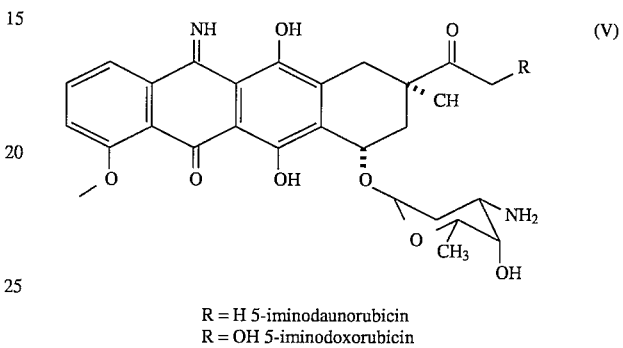

R = H 5-iminodaunorubicin
R = OH 5-iminodoxorubicin 5-iminodaunorubicin has a reduction potential of −0.675 while doxorubicin has a reduction potential of −0.625 Volts. Mitoxantrone has a reduction potential much more negative (−0.775 Volts) than doxorubicin, while ametantrone has a reduction potential of −0.68 Volts.

Also in the field of anthracenediones there have been many examples of chromophore modified analogues. Thiophene-analogues of mitoxantrone were expected to have a more negative reduction potential and therefore were expected to have potentially reduced cardiotoxic potential (Krapcho, A. P. et al., J. Med. Chem., 33, 2651–2655, (1990)). This is because the thiophene ring is more electron rich than the isosteric benzenoid ring present in the parent drugs. 10-imino-9-anthracenones have been prepared with the replacement of the quinone carbonyl by the imino group (Borowsky, E. et al., J. Med. Chem., 34, 541–546, (1991)). The synthesis of anthrapyrazoles is based on the same rationale of designing chromophore modified anthracenediones with reduced cardiotoxicity. In anthrapyrazoles not only the central quinone ring was modified to a quasi imino-quinone, but also, in contrast to the chromophore-modified anthracyclines, this strategy incorporated another ring into the chromophore. Studies of the biochemical pharmacology of the anthrapyrazoles suggest that the anthrapyrazoles may have a low potential for cardiotoxicity relative to doxorubicin and mitoxantrone. The compounds induce far less superoxide dismutase sensitive oxygen consumption than does doxorubicin when incubated with a rat liver microsomal preparation. These findings are in agreement with the polarographic properties of selected anthrapyrazoles that show a much greater resistance to reduction ($E_{1/2}$ from −0.983 to −1.085 V) relative to daunorubicin ($E_{1/2}$=−0.625 V) and mitoxantrone ($E_{1/2}$=−0.775 V). (Data from Showalter et al, Anti-Cancer Drug Design, (1986) Vol.1, pp.73–85).

Aza-anthracenediones (VI) are reported by P. Krapcho in J. Med. Chem., 28, 1124–26, (1985). They were prepared with the aim to provide analogues with reduced cardiotoxiciy potential. However the compounds are reported to possess a less negative reduction potential than mitoxantrone and therefore they do not seem to be promising. The less negative reduction potential of compound VI is a logical consequence of the substitution of the carbocyclic ring with the electron deficient pyridine ring.

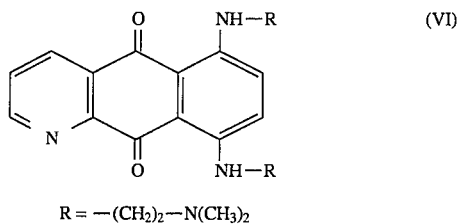

R = —(CH$_2$)$_2$—N(CH$_3$)$_2$

More recently other research groups have postulated that the electron affinity of quinone anticancer drugs is not the sole factor responsible for cardiotoxicity. They rather suggest that the most important determinant in establishing cardiotoxic side effects is the affinity displayed by these drugs for certain enzymes which are responsible for their in vivo reduction. These enzyme-substrate properties seem to be the major factor in stimulating oxygen radical production. In light of this rationale, chemical modifications should be rather addressed at modifying functional groups responsible for enzyme affinity and not at lowering reduction potential. A number of functional groups has been identified which are essential for the affinity of anthracenediones to NADH dehydrogenase (the enzyme responsible for mitochondrial reduction of anthraquinones): among these the presence of both quinone carbonyl groups is indispensable. The substitution of one carbonyl by an imino group results in the decrease of substrate affinity and this seems to be the reason for the reduced peroxidating activity of anthrapyrazoles (Stefanska, B. et al., 6-[(aminoalkyl)amino]-substituted 7H-benzo[e]pyrimidin-7-ones as Novel Antineoplastic Agents. Synthesis and Biological Evaluation, J. Med. Chem., 36, 38–41, (1993)).

A third hypothesis has recently been developed. The presence in both mitoxantrone and doxorubicin of adjacent hydroxyl and quinone groups has been noticed as a structural feature that can facilitate metal binding. Formation of a drug-metal complex could thereby enhance oxidation-reduction cycling by a metal-catalyzed type reaction (Shipp, N. G. et al., Characterization of Experimental Mitoxantrone Cardiotoxicity and its Partial Inhibition by ICRF-187 in Cultured Neonatal Rat Heart Cells, Cancer Research, 53, 550–6, (1993)).

Despite the proliferation of theories to explain the cardiotoxicity of anthracene antitumor agents, no compounds have been shown to possess both good anti-tumor activity and little or no cardiotoxicity. One could therefore conclude that there is not any convincing hypothesis that can alone account for reduced cardiotoxicity of quinone anticancer drugs and there is consequently no way to predict what compounds will cause carditoxicity and what compounds will not cause cardiotoxicity. This in light of the disappointing results so far obtained given that also heteroanalogues of anthracenediones, such as anthrapyrazoles, have shown to induce irreversible cardiotoxicity (Vandenberg, T. et al., A Phase II Study of DUP-941 in Advanced Breast Cancer Patients with No Prior Chemotherapy, Abs. No. 10, in Chemotherapy Foundation Symposium XI: Innovative Cancer Chemotherapy for Tomorrow, Nov. 10–12, 1993).

SUMMARY OF THE INVENTION

Applicants have discovered that 6,9-bis[(2-aminoethyl)amino]benzo[g]isoquinoline-5,10-dione and its bis-maleate salt are devoid of cardiotoxic effects.

SYNTHESIS OF THE COMPOUND OF THE INVENTION

The compound of the invention, 6,9-bis[(2-aminoethyl)amino]benzo[g]isoquinoline-5,10-dione dimaleate, can be made by several prior art methods such as those disclosed in WO 92/15300 and in the following paper: A. P. Krapcho et al. "6,9-bis[(2-aminoalkyl)amino]benzo[g]isoquinoline-5, 10-diones. A novel class of chromophore-modified antitumor anthracene-9,10-diones: synthesis and antitumor evaluations", J. Med. Chem. (1994) in press. However the most preferred method of synthesis is disclosed in related application Ser. No. 08/220,007, attorney docket number P1580-4004 (herein incorporated by reference) which results in production of the compound in very high purity.

Preparative Example redox potentials

Figure 1:
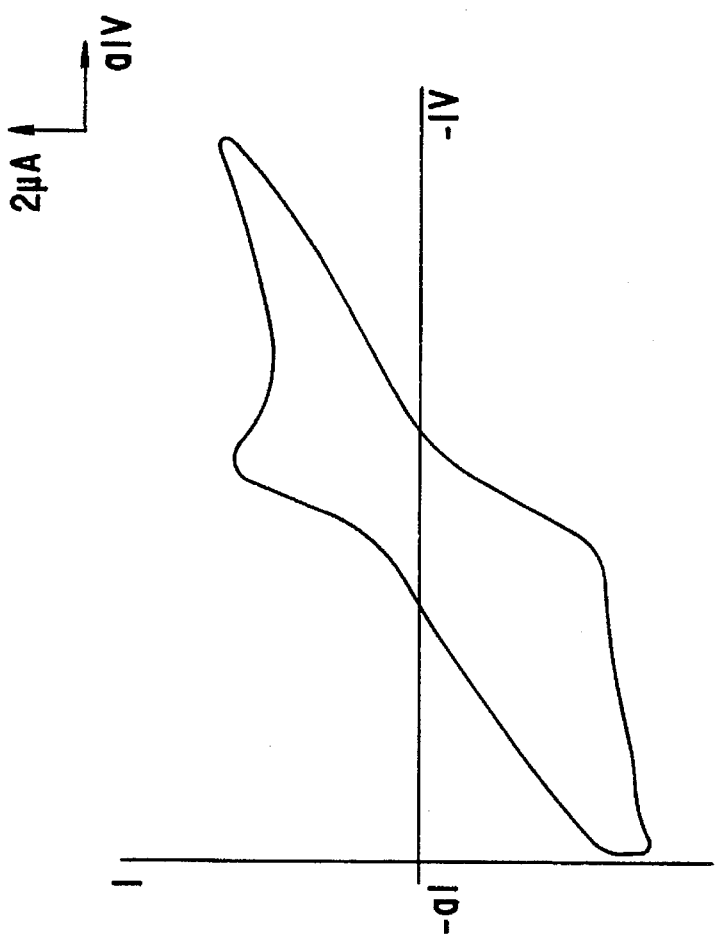
FIG. 1. Cyclic voltammetry of the compound of the invention in aqueous media.

The anthracene 9,10-dione moiety is known to undergo redox processes. The results of cyclic voltammetry measurements in aqueous media are reported in FIG. 1 and summarized as reduction potentials in Table 1. The redox process of (6,9-bis[(2-aminoethylamino]-benzo[g]isoquinoline-5,10-dione dimaleate is reversible, hence permanent modifications of the molecule as a result of redox cycling are not expected, unless the intermediates are trapped in their reactive form by enzymatic systems. The reduction potential for BBR 2778 appears to be 0.2–0.3 V lower than for mitoxantrone which means that reduction is substantially easier for BBR 2778. This means that a higher quantity of BBR 2778 can undergo enzymatic reduction "in vivo" than mitoxantrone. Moreover, since BBR 2778 has a cyclic voltammetry profile, its reduction product could be reoxidized again to BBR 2778, which therefore can act as a free radical propagator.

Cyclic voltammetry

Cyclic voltammetry (CV) measurements were performed at room temperature using an Amel scanning potentiostat at the following settings: Initial potential −0.1 V, switching potential 1 V, scan rate 0.4 V/s. A three electrode system was used with a reference saturated calomel electrode and a platinum wire counter electrode; a hanging mercury drop electrode (HMDE, Metrohm) was the working electrode.

TABLE 1

| COMPOUND | $E_{1/2}$ |
| --- | --- |
| Mitoxantrone | −0.74 |
| Ametantrone | −0.68 |
| 6,9-bis[(2-aminoethyl-amino]-benzo[g]isoquinoline-5,10-dione dimaleate | −0.54 |

TREATMENT

The compounds of the present invention may be used as active ingredient of therapeutic compositions to induce regression and/or palliation of cancers in mammals when administered in amounts ranging from about 0.02 mg to about 100 mg per kilogram of body weight. A preferred dosage regimen in the human would be from 0.2 to 2 mg/kg of body weight once every three weeks. Alternatively, another preferred dosage regimen in the human would be from 0.05 to 1.2 mg/kg of body weight once a week. The dosage may be adjusted to be compatible to other treatment regimens, such as radiation therapy.

The pharmaceutical compositions may be in the form of tablets, capsules, gel capsules, suppositories, lyophilized powders, and solutions for intravenous administration.

STUDIES ON POTENTIAL CARDIOTOXICITY OF 6,9-bis[(2-aminoethyl)amino]benzo[g]isoquinoline-5,10-dione dimaleate (BBR 2778)

Preliminary evaluation of potential cardiotoxicity in the mouse in comparison with mitoxantrone During an antitumor activity experiment histopathologic examination was carried out on plastic sections (blue toluidine stained) of hearts of some animals sacrificed at the end of the observation period.

In this experiment (Table 2) $CD_1$ Nu/Nu female mice (8 animals/groups) were transplanted sc with tumor fragments of human mammary carcinoma MX-1. BBR 2778 (60 mg/kg/day) and mitoxantrone (4.5 mg/kg/day) (i.e., at their equiactive doses) were i.v. given once a week for three weeks when tumor weight reached an average of 100–200 mg; animals were sacrificed 60 days after the last treatment.

Myocardial lesions were scored according to Bertazzoli, C. et al. (1979) Cancer Treat., Rep.: 63, 1877–1883. Briefly, lesions are scored as follows:

Severity Degree
1: sarcoplasmatic microvacuolizations and/or inclusions, and either interstitial or cellular edema;
2: as in 1 plus either sarcoplasmatic macrovacuolizations or one or more of atrophy, necrosis, fibrosis, endocardial lesions and thrombi;

Extension Degree
0: no lesions;
0.5: less than 10 single altered myocytes in the whole heart section;
1: scattered single altered myocytes (>10);
2: scattered small groups of altered myocytes;
3: widely spread small groups of altered myocytes;
4: confluent groups of altered myocytes;
5: most cells damaged.

The product of severity degree (1 or 2) times the extension degree (from 0 to 5) gives the T.C.S. (total cardiotoxicity score, graded from 0 to 10) for each animal. Mean Total Score (M.T.S.) for each group is calculated from T.C.S. of all the group animals. Results, reported as group-Mean-Total-Score (M.T.S.) are shown in Table 2.

On the basis of the obtained results, one can assess that:

BBR 2778 does not exert significant cardiotoxicity patterns when administered with the protocol used to test antitumor activity; on the contrary, mitoxantrone, under the same experimental conditions, is strongly cardiotoxic at equiactive doses.

TABLE 2

HISTOPATHOLOGICAL EVALUATION OF POTENTIAL CARDIOTOXIC EFFECT OF BBR 2778 AND MITOXANTRONE IN NUDE MICE (IV q7d × 3) DURING ANTITUMOR ACTIVITY TESTS

| Treatment Group | Dose (mg/kg/day) | No. affect. hearts No. exam. hearts | M.T.S |
|---|---|---|---|
| Control | — | 0/3 | 0 |
| BBR 2778 | 60 | 3/4 | 0.4 |
| Mitoxantrone | 4.5 | 5/5 | 6.8 |

M.T.S. = (group) Mean Total Score
Note: Affected hearts in BBR 2778 treated animals always scored a T.C.S. (individual Total Cardiotoxic Score) equal to or lower than 0.5.

Pivotal Cardiotoxicity Studies of 6,9-bis[(2-aminoethyl)amino]benzo[g]isoquinoline-5,10-dione dimaleate in the Mouse and in the Rat in Comparison with Reference Standards In the rat (Study No. 1, Table No. 3), the respective effects on the myocardium of BBR 2778 and mitoxantrone were compared. Both drugs were i.v. administered in single equitoxic doses (LD10). In the mouse (Study No. 2, Table No. 4), the respective effects on the myocardium of BBR 2778, mitoxantrone, and doxorubicin, using multiple i.v. equiactive doses with similar activity on solid tumors, were compared. Also in the mouse, in a different study (Study No. 3, Table No. 5), the respective effect on the myocardium of i.v. BBR 2778 dose-active range on murine leukemia was compared with mitoxantrone. Results of those studies are given in Tables 3, 4, and 5.

Cardiac lesions in the three studies were evaluated in accordance with a qualitative/quantitative method expressly devised for anthracyclines (Bertazzoli C. et al. Cancer Treat. Rep. 63:1877–1883, 1979; Solcia E. et al. Tumori, 67:461–472, 1981).

CARDIOTOXICITY—METHODOLOGY (STUDY No. 1)

| | |
|---|---|
| Species: | rat |
| Strain: | S.D. (Crl:CDBR) |
| Sex: | male |
| Age: | 8 weeks |
| Weight: | 175–200 g |
| Compounds: | BBR 2778   65.1 mg/kg |
| | mixtoxantrone   4.9 mg/kg |
| | water (control group)   4 ml/kg/day |
| Day of treatment: | 1 |
| Parameters evaluated: | heart weight and microscopic lesions |
| Histopathology: | paraffin sections of heart (formalin fixed and haematoxilineos in stained) collected 6 weeks from treatment |
| Morphological evaluation of cardiac lesions: | the product of severity degree (1 or 2) times the extension degree (from 0 to 5) gives the T.C.S. (Total Cardiotoxicity Score, graded from 0 to 10) for each animal. M.T.S. (Mean Total Score) for each group is calculated from the T.C.S. of all the group animals. |

TABLE 3

SINGLE DOSE CARDIOTOXICITY IN I.V. TREATED RATS: MORPHOLOGICAL EVALUATION OF CARDIAC LESIONS

| Treatment Group | Dose (mg/kg) | Heart Weight (%) | No. affect. hearts No. exam. hearts | M.T.S |
|---|---|---|---|---|
| 0 Control | — | 100 | 1/10 | 0 |
| 1 Mitoxantrone | 4.9 | −44 | 7/7 | 6 |
| 2 BBR 2778 | 65.1 | −6 | 1/9 | 0 |

CARDIOTOXICITY—METHODOLOGY (STUDY. No. 2)

| | |
|---|---|
| Species: | mouse |
| Strain: | C57BL/6NCrlBR) |
| Sex: | female |
| Age: | 5 weeks |
| Weight: | 18–20 g |
| Compounds: | BBR 2778   40 and 60 mg/kg/day |
| | mixtoxantrone   3 and 4 |

|  |  | mg/kg/day |
| --- | --- | --- |
|  | doxorubicin | 6 and 7.5 mg/kg/day |
|  | water (control group) | 10 ml/kg/day |
| Days of treatment: | 1, 8, 15 and 22 | |
| Parameters evaluated: | heart weight and microscopic lesions | |
| Histopathology: | plastic sections of heart (formalin fixed and blue toluidine stained) collected 60 and 90 days from the first treatment | |
| Morphological evaluation of cardiac lesions: | the product of severity degree (1 or 2) times the extension degree (from 0 to 5) gives the T.C.S. (Total Cardiotoxicity Score, graded from 0 to 10) for each animal. M.T.S. (Mean Total Score) for each group is calculated from the T.C.S. of all the group animals. | |

TABLE 4

MULTIPLE DOSE CARDIOTOXICITY IN I.V. TREATED MICE: MORPHOLOGICAL EVALUATION OF CARDIAC LESIONS

| Group | Dose (mg/kg) | Cumulative Dose (mg/kg) | 60 days after first administration | | 90 days after first administration | |
| --- | --- | --- | --- | --- | --- | --- |
|  |  |  | No. affect. hearts No. exam. hearts | M.T.S. | No. affect. heart No. exam. hearts | M.T.S. |
| 0 Control | — | — | 0/6 | 0 | 1/6 | 0.1 |
| 1 Doxorubicin | 6 | 24 | 6/6 | 1 | 6/6 | 1.1 |
| 2 Doxorubicin | 7.5 | 30 | 6/6 | 1.5 | 6/6 | 2.2 |
| 3 Mitoxantrone | 3 | 12 | 6/6 | 1.4 | 5/5 | 2.6 |
| 4 Mitoxantrone | 4 | 16 | 6/6 | 1.25 | 6/6 | 2.5 |
| 5 BBR 2778 | 40 | 160 | 0/6 | 0 | 5/6 | 0.4 |
| 6 BBR 2778 | 60 | 240 | 1/6 | 0.1 | 0/2 | 0 |

Note: Affected hearts in BBR 2778 treated animals always scored a T.C.S. (individual Total Cardiotoxic Score) equal to or lower than 0.5.

CARDIOTOXICITY—METHODOLOGY (STUDY No. 3)

| Species: | mouse | |
| --- | --- | --- |
| Strain: | CD1 | |
| Sex: | female | |
| Age: | 5 weeks | |
| Weight: | 19–21 g | |
| Compounds: | BBR 2778 | 12, 19.5 & 27 mg/kg/day |
|  | mixtoxantrone | 1.1, 1.8 & 2.5 mg/kg/day |
|  | water (control group) | 10 ml/kg/day |
| Treatment: | twice a week for 5 weeks (10 dosing) low- and mid- dose treated groups; twice a week for 4 weeks (7 dosing) in high-dose treated groups. In these groups, the administration was suspended because of the high mortality rate recorded in mitoxantrone high-dose treated group. | |
| Weeks of Treatment: | 1, 2, 5, 6 and 7 | |
| Parameters evaluated: | microscopic lesions | |
| Histopathology: | plastic sections of heart (formalin fixed and blue toluidine stained) collected 78 and 139 days from the first administration | |
| Morphological evaluation of cardiac lesions: | the product of severity degree (1 or 2) times the extension degree (from 0 to 5) gives the T.C.S. (Total Cardiotoxicity Score, graded from 0 to 10) for each animal. M.T.S. (Mean Total Score) for each group is calculated from the T.C.S. of all the group animals. | |

TABLE 5

MULTIPLE DOSE CARDIOTOXICITY IN I.V. TREATED MICE: MORPHOLOGICAL EVALUATION OF CARDIAC LESIONS: MTS = GROUP MEAN TOTAL SCORE

| Group | Dose (mg/kg) | Cumulative Dose (mg/kg) | 78 days after first administration | | 139 days after first administration | |
|---|---|---|---|---|---|---|
| | | | No. affect. hearts No. exam. hearts | M.T.S. | No. affect. heart No. exam. hearts | M.T.S. |
| 1 Control | — | — | 0/8 | 0 | 1*/6 | 0.1 |
| 2 Mitoxantrone | 1.1 | 11 | 8°/8 | 4 | 9°/9 | 6 |
| 3 Mitoxantrone | 1.8 | 18 | 4°/4 | 6.5 | 1♦/1 | — |
| 4 Mitoxantrone | 2.5 | 17.5 | 11°/11 | 7.1 | 0/0 | — |
| 5 BBR 2778 | 12 | 120 | 4*/7 | 0.3 | 5*/10 | 0.3 |
| 6 BBR 2778 | 19.5 | 195 | 4*/10 | 0.2 | 1*/7 | 0.1 |
| 7 BBR 2778 | 27 | 189 | 6*/11 | 0.2 | 1*/10 | 0.1 |

♦) Total cardiotoxicity score = 8
°) Total cardiotoxicity score = 3–8
*) Total cardiotoxicity score = 0.5

MYELOTOXICITY STUDIES

Using CD2F1 mice, the respective effects on the bone marrow of BBR 2778 and mitoxantrone were compared. The drugs were administered i.v. in multiple doses. The dose and treatment schedule employed had been shown to be equally effective in previous antitumor activity studies against leukemia in mice of the given strain for both compounds.

MYELOTOXICITY—METHODOLOGY

| | |
|---|---|
| Species: | mouse |
| Strain: | CD2F1 |
| Sex: | male |
| Age: | 6 weeks |
| Weight: | 19–20 g |
| Compounds: | BBR 2778  12 mg/kg/day |
| | mixtoxantrone  3 mg/kg/day |
| | water (control group)  10 ml/kg/day |
| Day of treatment: | 1, 4 and 7 |
| Sampling site: | orbital sinus |
| Sampling days: | 6, 9, 11, 13, 15, 19, 22, 25 and 28 |
| Parameters: | red blood cells (RBC), white blood cells (WBC), platelet (PLT) |
| Equipment: | Delcon Cellanalyzer CA580A |

Figure 2:
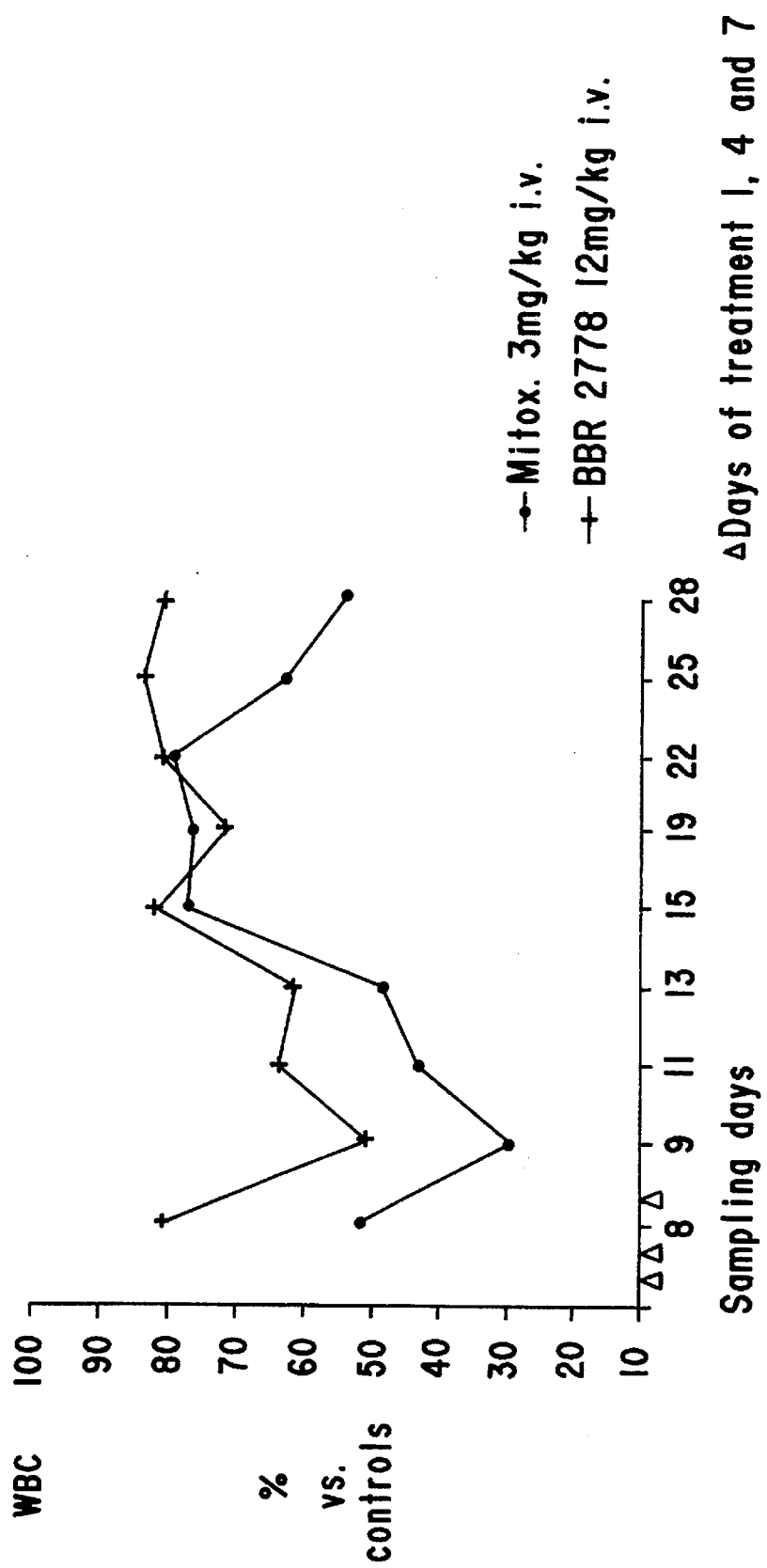
FIG. 2. Myelotoxicity of the compound of the invention.

Results (FIG. 2):

On the basis of RBC, WBC and PLT count, mitoxantrone induced (at the tested doses and at nadir day) more marked leukopenia (70% vs. controls) than BBR 2778 tested at equiactive dosage (50% vs. controls).

We claim:

1. A method of treatment of tumors susceptible to azaanthracene-dione therapy in a mammal requiring such treatment, which method causes minimal cardiotoxicity, comprising administering to the mammal an effective anti-tumor amount of the compound 6,9-bis[(2-aminoethyl)-amino]-benzo[g]isoquinoline-5,10-dione or a physiologically acceptable salt thereof wherein the mammal has been previously treated with mitoxantrone, doxorubicin, or any other anthracycline used in human therapy and has shown cardiotoxicity with said prior treatment.

2. The method of claim 1 wherein the compound is 6,9-bis[(2-aminoethyl)-amino]-benzo[g]isoquinoline-5,10-dione dimaleate.

3. The method of claim 1 wherein the dosage regimen is from 0.2 to 2.0 mg/kg of body weight once every three weeks.

4. The method of claim 1 wherein the dosage regimen is from 0.05 to 1.2 mg/kg of body weight once every week.

* * * * *